US005955456A

United States Patent [19]

Prato et al.

[11] Patent Number: 5,955,456

[45] Date of Patent: Sep. 21, 1999

[54] INJECTABLE PHARMACEUTICAL COMPOSITION COMPRISING URSODESOXYCHOLIC ACID OR TAUROURSODESOXYCHOLIC ACID, A STRONG BASE AND TROMETHAMOL

[75] Inventors: Tiziano Prato, Varese; Anna Giulia Rusticali, Glorie, both of Italy

[73] Assignee: Sanofi, Paris, France

[21] Appl. No.: 09/091,706

[22] PCT Filed: Dec. 26, 1996

[86] PCT No.: PCT/FR96/02083

§ 371 Date: Jun. 23, 1998

§ 102(e) Date: Jun. 23, 1998

[87] PCT Pub. No.: WO97/24125

PCT Pub. Date: Jul. 10, 1997

[30] Foreign Application Priority Data

Dec. 27, 1995 [IT] Italy ................................ MI95A2763

[51] Int. Cl.$^{6}$ .................................................. A61K 31/575

[52] U.S. Cl. ........................................................... 514/182

[58] Field of Search ..................................... 514/182, 664

[56] References Cited

U.S. PATENT DOCUMENTS 4,649,155 3/1987 Steffen et al. .......................... 514/458

FOREIGN PATENT DOCUMENTS 086705 8/1983 European Pat. Off. .
285285 10/1988 European Pat. Off. .
692487 1/1996 European Pat. Off. .

*Primary Examiner*—James H. Reamer
*Attorney, Agent, or Firm*—Michael D. Alexander; Paul E. Dupont

[57] ABSTRACT

Injectable aqueous composition comprising ursodeoxycholic acid or tauroursodeoxycholic acid, a strong base compatible with intravenous injection and trometamol.

14 Claims, No Drawings

INJECTABLE PHARMACEUTICAL COMPOSITION COMPRISING URSODESOXYCHOLIC ACID OR TAUROURSODESOXYCHOLIC ACID, A STRONG BASE AND TROMETHAMOL

The present invention relates to a novel pharmaceutical composition based on ursodeoxycholic acid, either as such or conjugated with taurine.

In particular, the invention relates to an injectable formulation of ursodeoxycholic acid or tauroursodeoxycholic acid for intravenous administration, especially by slow perfusion.

Ursodeoxycholic acid and tauroursodeoxycholic acid are drugs which are widely used in therapy as litholytics and in the treatment of various pathological conditions of the liver, such as hepatic cholestasis and primary biliary cirrhosis. It has now been found that the action of these drugs is also particularly useful in the treatment of pathological conditions of the liver in patients for whom oral administration is impossible or difficult.

No injectable pharmaceutical formulations based on ursodeoxycholic acid or tauroursodeoxycholic acid are currently available on the market because their preparation presents problems due to the physicochemical properties of these active principles.

Ursodeoxycholic acid is a weak acid which is practically insoluble in water; its solubility increases greatly in the presence of strong bases such as sodium hydroxide and potassium hydroxide. However, aqueous solutions consisting solely of ursodeoxycholic acid and a strong base are not suitable for intravenous administration because even a small variation in the amount of strong base in the preparation leads to a consequent variation in the pH of the injectable solution which is often incompatible with intravenous administration.

In contrast to ursodeoxycholic acid, tauroursodeoxycholic acid is a strong acid which is soluble in water, its pKa being about 1.4. This strong acidity is incompatible with intravenous administration; in this case too, it is possible to resort to the addition of bases to the solution, although the above-mentioned problems of pH variation still remain unsolved.

Also, ursodeoxycholic and tauroursodeoxycholic acids are detergent compounds and, for this reason, cause foaming when added to an aqueous solution such as the solution for intravenous perfusion.

It has now been found that the addition of trometamol ((trishydroxymethyl)aminomethane) to an aqueous solution containing ursodeoxycholic acid or tauroursodeoxycholic acid and strong bases produces stable, well-buffered solutions suitable for intravenous administration.

It has moreover been observed that the addition of trometamol surprisingly reduces foaming and the persistence of the foam which forms in the solution for intravenous perfusion following the addition of the above preparation.

The present invention therefore relates to an injectable aqueous composition which comprises ursodeoxycholic acid or tauroursodeoxycholic acid, a strong base compatible with intravenous administration, and trometamol.

According to the present invention, the water used is suitable for injectable preparations.

The formulation according to the invention comprises an amount of active principle—ursodeoxycholic acid or tauroursodeoxycholic acid—of between 1 and 30% (w/v) and preferably of between 5 and 20% (w/v), for example 10% (w/v).

The strong base compatible with intravenous administration is preferably sodium or potassium hydroxide; such bases are used in a stoichiometrically equivalent amount relative to the acid employed.

The trometamol is added at a rate of 0.01–2% (w/v), preferably at a rate of about 0.1% (w/v).

The formulation according to the invention advantageously consists of an aqueous solution which comprises from 5 to 15% (w/v) of active principle (ursodeoxycholic acid or tauroursodeoxycholic acid), a stoichiometrically equivalent amount of strong base (sodium or potassium hydroxide) and from 0.05 to 0.2% (w/v) of trometamol, ursodeoxycholic acid being the preferred active principle.

The injectable aqueous formulation forming the subject of the present invention preferably contains about 10% (w/v) of ursodeoxycholic acid, about 1% (w/v) of sodium hydroxide and about 0.1% (w/v) of trometamol.

The formulation of the present invention is prepared by separately mixing the different components with distilled water and subsequently combining the solutions/suspensions obtained. It is therefore appropriate to filter the solution in order to remove any residues, and sterilize it.

Preferably, before sterilization, which is performed in an autoclave, the solution is subdivided into ampoules or single-dose bottles, this operation optionally being carried out under a nitrogen atmosphere, and, when it is used, it is diluted in the solution for intravenous perfusion in order to be administered by slow perfusion.

If it were desired to use multi-dose containers, it could be appropriate to add a bactericide to the composition.

A particularly advantageous solution for intravenous perfusion is the (conventional) isotonic solution (containing 0.9% of sodium chloride).

Isotonic solutions for intravenous perfusion which contain the above composition are also a subject of the present invention.

More particularly, the invention further relates to a composition for intravenous perfusion which comprises isotonic solution, ursodeoxycholic acid or tauroursodeoxycholic acid, a strong base compatible with intravenous administration in a stoichiometrically equivalent amount relative to the acid employed, and trometamol.

According to another of its aspects, the present invention relates to the use of ursodeoxycholic acid or tauroursodeoxycholic acid for the preparation of injectable formulations suitable for the treatment of pathological conditions of the liver in patients for whom the oral administration of drugs is impossible.

Said formulations are useful in subjects who have undergone a transplant (for example liver, heart, bone marrow, kidney) in order to combat the hepatotoxic effects of the drugs which are normally administered following the transplant intervention; in subjects suffering from hepatic insufficiency; in subjects who are being fed entirely by the parenteral route; in subjects who have undergone a massive intestinal resection which requires an extended fast; and in newborns and children suffering from hepatic cholestasis.

The duration of the treatment involving the slow intravenous perfusion of ursodeoxycholic acid or tauroursodeoxycholic acid, administered preferably by means of the formulation forming the subject of the invention, varies according to the pathological conditions to be treated. In general, said duration varies from 1 to 30 days, advantageously from 3 to 10 days and preferably from 5 to 7 days. Several treatment cycles can be carried out if necessary.

Of course, the daily dose of active principle to be administered varies according to the patient's age and weight and according to the type and severity of the pathological condition to be treated.

In general, the daily dose of active principle to be administered according to the present invention (expressed in mg of acid) is between 2 and 30 mg/kg body weight, advantageously between 4 and 20 mg/kg and preferably between 8 and 15 mg/kg. For an adult of normal constitution, the daily dose is between 500 and 2000 mg.

The unit doses can therefore contain from 100 to 2000 mg of active principle (expressed in mg of acid). After appropriate dilution in the solution for intravenous perfusion, said unit doses can be administered 1 or more times a day, as required.

According to one preferred aspect, the unit doses contain 250 or 500 mg of active principle (expressed in mg of acid) in volumes of 2.5 and 5 ml respectively.

The Example which follows illustrates the invention more clearly.

EXAMPLE 1

INJECTABLE COMPOSITION BASED ON 10% URSODEOXYCHOLIC ACID—Ampoules containing 250 mg of ursodeoxycholic acid A solution of 20 g of sodium hydroxide in 200 ml of distilled water and a solution of 2 g of trometamol in 50 ml of distilled water are added to a suspension of 200 g of ursodeoxycholic acid in 1300 ml of distilled water. If appropriate, a few drops of 1N aqueous sodium hydroxide solution are added to the resulting mixture until it becomes clear. It is diluted with distilled water qsp ad 2000 ml. It is filtered through a Millipore® HAWP 0.45 $\mu$ membrane+ Millipore® AP25 prefilter. Under a nitrogen atmosphere the solution obtained is divided up into 800 ampoules of neutral white glass for injectable compositions, 2.5 ml of solution being poured into each ampoule. The ampoules are sterilized in an autoclave at 121° C. for 30 minutes.

The ampoules obtained in this way are suitable for dilution in an isotonic solution and administration by slow perfusion.

EXAMPLE 2

INJECTABLE COMPOSITION BASED ON 10% URSODEOXYCHOLIC ACID—Ampoules containing 500 mg of ursodeoxycholic acid The title composition is obtained by following the procedure described in Example 1 except that 5 ml of solution are poured into 400 ampoules.

We claim:

1. An injectable aqueous composition which comprises ursodeoxycholic acid or tauroursodeoxycholic acid, a strong base compatible with intravenous administration, and trometamol.

2. A composition according to claim 1 wherein the active principle is present in an amount of between 1 and 30% (w/v).

3. A composition according to claim 1 wherein the strong base is sodium or potassium hydroxide.

4. A composition according to claim 3 wherein the strong base is present in an amount stoichiometrically equivalent to the active principle.

5. A composition according to claim 1 wherein the trometamol is present at a rate of 0.01–2% (w/v).

6. A composition according to claim 1 which comprises from 5 to 15% (w/v) of ursodeoxycholic acid, a stoichiometrically equivalent amount of a strong base selected from sodium or potassium hydroxide and from 0.05 to 0.2% (w/v) of trometamol.

7. A composition according to claim 6 which comprises about 10% (w/v) of ursodeoxycholic acid, about 1% (w/v) of sodium hydroxide and about 0.1% (w/v) of trometamol.

8. A composition according to claim 7 wherein said composition is subdivided into unit doses containing 250 or 500 mg of ursodeoxycholic acid.

9. A method for the treatment of pathological conditions of the liver in patients for whom the oral administration of drugs is impossible or difficult which comprises administering to a patient in need of such treatment a composition according to claim 1.

10. A method for the treatment of the hepatotoxic effects of the drugs which are normally administered following the transplant intervention in subjects who have undergone a transplant which comprises administering to a patient in need of such treatment a composition according to claim 1.

11. A method for the treatment of pathological conditions of the liver in subjects suffering from hepatic insufficiency; in subjects who are being fed entirely by the parenteral route; in subjects who have undergone a massive intestinal resection which requires an extended fast; and in newborns and children suffering from hepatic cholestasis which comprises administering to a patient in need of such treatment a composition according to claim 1.

12. A composition according to claim 1 wherein the active principle is present in an amount of between 5 and 20% (w/v).

13. A composition according to claim 1 wherein the active principle is present in an amount of about 10% (w/v).

14. A composition according to claim 1 wherein the trometamol is present at a rate of about 0.1% (w/v).

* * * * *